(12) United States Patent
Nakagawara et al.

(10) Patent No.: US 7,985,556 B2
(45) Date of Patent: Jul. 26, 2011

(54) METHOD OF SCREENING APOPTOSIS ACCELERATING COMPOUND OR ANTI-APOPTOTIC COMPOUND AND METHOD OF DETERMINING MALIGNANCY OF NEURODEGENERATIVE DISEASE

(75) Inventors: Akira Nakagawara, Chiba (JP); Toshinori Ozaki, Chiba (JP)

(73) Assignees: Hisamitsu Pharmaceutical Co., Inc., Saga (JP); Chiba Prefecture, Chiba (JP)

( * ) Notice: Subject to any disclaimer, the term of this patent is extended or adjusted under 35 U.S.C. 154(b) by 634 days.

(21) Appl. No.: 12/063,381

(22) PCT Filed: Aug. 9, 2006

(86) PCT No.: PCT/JP2006/315749
§ 371 (c)(1),
(2), (4) Date: Jun. 12, 2008

(87) PCT Pub. No.: WO2007/018238
PCT Pub. Date: Feb. 15, 2007

(65) Prior Publication Data
US 2010/0279312 A1    Nov. 4, 2010

(30) Foreign Application Priority Data

Aug. 11, 2005   (JP) ................ P2005-233429

(51) Int. Cl.
*G01N 33/53*   (2006.01)
*G01N 33/567*   (2006.01)
(52) U.S. Cl. ........................................ 435/7.1; 435/7.2
(58) Field of Classification Search ............ 435/7.1, 435/7.2
See application file for complete search history.

(56) References Cited

FOREIGN PATENT DOCUMENTS

| WO | 02/090549 A2 | 11/2002 |
|---|---|---|
| WO | 03/012102 A2 | 2/2003 |
| WO | 03/018842 A1 | 3/2003 |

OTHER PUBLICATIONS

Kou Miyazaki, et al., "NEDL1, a Novel Ubiquitin-protein Isopeptide Ligase for Dishevelled-1, Targets Mutant Superoxide Dismutase-1", The Journal of Biological Chemistry, 2004, pp. 11327 to 11335, vol. 279, No. 12.

Yili Yang, et al., "Small molecule inhibitors of HDM2 ubiquitin ligase activity stabilize and activate p53 in cells", Cancer Cell, Jun. 2005, pp. 547 to 559, vol. 7, No. 6.

Kou Miyazaki, et al., "A novel HECT-type E3 ubiquitin ligase, NEDL2, stabilizes p73 and enhances its transcriptional activity", Biochemical and Biophysical Research Communication, 2003, pp. 106 to 113, vol. 308, No. 1.

Daniel R. Rosen, et al., "Mutations in Cu/Zn superoxide dismutase gene are associated with familial amyotrophic lateral sclerosis", Letters to Nature, Mar. 1993, pp. 59 to 62, vol. 362, No. 3721.

*Primary Examiner* — Jacob Cheu
*Assistant Examiner* — Pensee Do
(74) *Attorney, Agent, or Firm* — Sughrue Mion, PLLC (57) ABSTRACT

Screening methods for determining pro-apoptotic compounds or anti-apoptotic compounds comprise measuring the interaction between p53 and NEDL1 in the presence and in the absence of a test compound, and comparing the strength of interaction between p53 and NEDL1 in the presence and in the absence of the test compound.

4 Claims, 10 Drawing Sheets

METHOD OF SCREENING APOPTOSIS ACCELERATING COMPOUND OR ANTI-APOPTOTIC COMPOUND AND METHOD OF DETERMINING MALIGNANCY OF NEURODEGENERATIVE DISEASE

TECHNICAL FIELD

The present invention relates to methods for screening pro- or anti-apoptotic compounds. It further relates to a method for determining the malignancy of neurodegenerative diseases.

BACKGROUND ART

Amyotrophic Lateral Sclerosis (ALS) is a neurodegenerative disease with poor prognosis, wherein muscular atrophy occurs by degeneration and deficit of motor neurons in the spine, motor cortex and brainstem. Familial ALS (Familial Amyotrophic Lateral Sclerosis: FALS) currently accounts for 5-10% of all ALS cases. The responsible gene in some families with FALS has been identified as the Cu/Zn superoxide dismutase (SOD1) gene, with approximately 20% of FALS cases being attributed to genetic mutation in SOD1.

SOD1 inactivates superoxide, an active oxygen species produced in cells during the course of aerobic metabolism. The aggregate theory, which holds that mutated SOD1 forms aggregates in cells and thereby exhibits cellular toxicity, has recently become the prevailing theory as the cause of FALS (Non-patent document 1).

The present inventors have identified NEDL1, a gene coding for E3 ubiquitin ligase having a HECT domain, as a novel gene that is highly expressed in human neuroblastoma groups with good prognosis and natural regression, compared to groups with poor prognosis. It has been demonstrated that NEDL1 has a function of physically binding with mutant SOD1, one of responsible gene products in FALS, inducing its ubiquitination and thus promoting degradation of mutant SOD1. The binding strength between NEDL1 and mutant SOD1 depends on the severity of the condition, while no binding is detected with wild SOD1. In addition, experiments in model mice and immunostaining of actual case patient cells have indicated that ubiquitinated mutant SOD1 and NEDL1 are accumulated in the aggregates. This strongly suggests that interaction between NEDL1 and mutant SOD1 plays an important role in the onset and progression of FALS, although the detailed molecular mechanism of neural cell death (apoptosis) by NEDL1 are still unclear (Patent document 1, Non-patent document 2).

[Patent document 1] International Patent Publication No. WO03/018842
[Non-patent document 1] Rosen DR et al., Nature, 364: 59-62 (1993)
[Non-patent document 2] Miyazaki K et al., J. Biol. Chem., 279: 11327-11335 (2004)

DISCLOSURE OF THE INVENTION

Problems to be Solved by the Invention

Elucidation of the molecular mechanism of neural apoptosis by NEDL1 and discovery of compounds that enhance or inhibit apoptosis is essential for the development of therapeutic and prophylactic agents for cancer and neurodegenerative diseases. It is therefore an object of this invention to elucidate the NEDL1-dependent molecular mechanism of apoptosis. It is another object of the invention to provide a method for screening pro- or anti-apoptotic compounds based on the elucidated molecular mechanism. It is still another object of the invention to provide a method for determining the malignancy of neurodegenerative diseases based on the elucidated molecular mechanism.

Means for Solving the Problems

The present inventors have conducted experiments including expression analysis of various genes in the context of apoptosis induced by cisplatin treatment, and as a result, have discovered that NEDL1, which catalyzes degradation of target proteins via ubiquitination, does not promote degradation of p53 but rather promotes its activation. This suggests the existence of a new control mechanism for p53 by NEDL1. Furthermore, activation of p53 by NEDL1 is possibly a molecular mechanism regulating neural cell death in neurodegenerative diseases including not only ALS but also Alzheimer's disease and Parkinson's disease. The present inventors have completed the invention based on this knowledge.

Specifically, the invention provides a method for screening pro-apoptotic compounds comprising: a step of measuring the interaction between p53 and NEDL1 in the presence and in the absence of a test compound; and a step of determining the test compound to be a pro-apoptotic compound if the interaction between p53 and NEDL1 in the presence of the test compound is stronger than the interaction between p53 and NEDL1 in the absence of the test compound. This screening method applies knowledge of the molecular mechanism whereby apoptosis is induced by formation of complexes of p53 and NEDL1 by their direct interaction. This is a new molecular mechanism that has been discovered by the present inventors, and the screening method allows pro-apoptotic compounds to be obtained that have totally different action mechanisms than those currently known. Such compounds can be applied as apoptosis accelerators or anticancer agents.

The invention further provides a method for screening pro-apoptotic compounds comprising: a step of culturing cells expressing p53 and NEDL1 in the presence and in the absence of a test compound; a step of measuring the interaction between p53 and NEDL1 in the cultured cells; and a step of determining the test compound to be a pro-apoptotic compound if the interaction between p53 and NEDL1 in the cultured cells in the presence of the test compound is stronger than the interaction between p53 and NEDL1 in the cultured cells in the absence of the test compound. This screening method allows pro-apoptotic compounds to be obtained which have totally different action mechanisms than those currently known, and the compounds can be applied as apoptosis accelerators and anticancer agents.

The invention still further provides a method for screening anti-apoptotic compounds comprising: a step of measuring the interaction between p53 and NEDL1 in the presence and in the absence of a test compound; and a step of determining the test compound to be an anti-apoptotic compound if the interaction between p53 and NEDL1 in the presence of the test compound is weaker than the interaction between p53 and NEDL1 in the absence of the test compound. This screening method applies knowledge of the molecular mechanism whereby apoptosis is induced by formation of complexes of p53 and NEDL1 by their direct interaction. This is a new molecular mechanism that has been discovered by the present inventors, and the screening method allows anti-apoptotic compounds to be obtained that have totally different action mechanisms than those currently known. Such compounds can be applied as apoptosis inhibitors or therapeutic agents for neurodegenerative diseases.

The invention yet further provides a method for screening anti-apoptotic compounds comprising: a step of culturing cells expressing p53 and NEDL1 in the presence and in the absence of a test compound; a step of measuring the interaction between p53 and NEDL1 in the cultured cells; and a step of determining the test compound to be an anti-apoptotic compound if the interaction between p53 and NEDL1 in the cultured cells in the presence of the test compound is weaker than the interaction between p53 and NEDL1 in the cultured cells in the absence of the test compound. This screening method allows anti-apoptotic compounds to be obtained which have totally different action mechanisms than those currently known, and the compounds can be applied as apoptosis inhibitors and therapeutic agents for neurodegenerative diseases.

The invention yet further provides a method for determining the malignancy of neurodegenerative diseases comprising: a step of measuring the interaction between p53 and NEDL1 in neurons taken from a neurodegenerative disease subject; and a step of determining the malignancy of the neurodegenerative disease to be higher with stronger interaction between p53 and NEDL1. This determining method is based on knowledge of the molecular mechanism whereby apoptosis is induced by formation of complexes of p53 and NEDL1 by their direct interaction. This is a new molecular mechanism that has been discovered by the present inventors, whereby the malignancy of neurodegenerative diseases can be determined by different criteria than those currently known, and the determining method can be used for subject prognosis.

Effect of the Invention

The screening method of the invention allows pro-apoptotic compounds and anti-apoptotic compounds to be obtained which have totally different action mechanisms than those currently known. The discovery of such compounds will make possible the development of drugs effective for treatment and prevention of cancer and neurodegenerative diseases (ALS, Alzheimer's disease, Parkinson's disease and the like).

In addition, the method of determining malignancy of neurodegenerative diseases according to the invention allows determination of the malignancy of neurodegenerative diseases by different criteria than those currently used.

BRIEF DESCRIPTION OF THE DRAWINGS

FIG. 4(a) shows the appearance of the colonies and (b) is a graph showing the number of G418-resistant colonies.

FIG. 5(a) shows the appearance of the colonies and (b) is a graph showing the number of G418-resistant colonies.

FIG. 6(a) shows the appearance of the colonies and (b) is a graph showing the number of G418-resistant colonies.

FIG. 7(a) shows the results using $p21^{WAF1}$ luciferase reporter, and (b) shows the results using Bax luciferase reporter.

BEST MODE FOR CARRYING OUT THE INVENTION

Preferred embodiments of the invention will now be described in detail.

(Methods for Screening Pro-Apoptotic Compounds)

One method for screening pro-apoptotic compounds according to the invention comprises a step of measuring the interaction between p53 and NEDL1 in the presence and in the absence of a test compound, and a step of determining the test compound to be a pro-apoptotic compound if the interaction between p53 and NEDL1 in the presence of the test compound is stronger than the interaction between p53 and NEDL1 in the absence of the test compound. Specifically, the "interaction" between p53 and NEDL1 refers to their binding to form a complex. Measurement of the interaction may employ a system for measurement of protein-protein interaction that is known to those skilled in the art, and for example, it may be a yeast two-hybrid assay or PCA (Protein Fragment Complementation Assay) method. The yeast two-hybrid and PCA methods are carried out in the manner described below.

The yeast two-hybrid method will be explained first. Yeast Gal4 is a transcription factor comprising an N-terminal DNA-binding domain (DBD) and a C-terminal transcription activation domain (AD). Both domains function essentially autonomously and the DBD can bind to DNA by itself, though without activating transcription. AD is the converse. A yeast two-hybrid assay was developed by applying these properties. Specifically, a fusion protein (bait) of the protein P of interest with Gal4 DBD and a fusion protein (prey) of another protein Q with Gal4 AD are introduced into yeast cells. If the proteins P and Q interact with each other in the nucleus, a transcriptional regulation complex is reconstituted in the yeast cell, resulting in activation of transcription dependent on a binding site for Gal4. The interaction between the proteins P and Q can be easily evaluated by using reporter genes to detect the activity. For example, HIS3, lacZ and URA3 can be utilized as reporter genes. Systems using SRF or LexA are also available in addition to yeast Gal4.

The screening method of the present invention may be performed by a system using p53 as the protein P and NEDL1 as the protein Q (the converse is also possible) in the yeast two-hybrid assay. Specifically, yeasts are allowed to express either p53 or NEDL1 as bait and the other as prey and cultured both in the presence and in the absence of a test compound. The respective transcriptional activities (which represent the strength of interaction between p53 and NEDL1) of reporter genes in the cultured yeasts are assayed. The test compound can be determined as a pro-apoptotic compound if the transcriptional activity in the presence of the test compound is greater than the transcriptional activity in the absence of the test compound.

A PCA assay will now be described. In the PCA assay, one functional protein A (e.g., an enzyme or transcription factor) is split into two fragments A1 and A2 which are then respectively fused with the proteins P and Q of interest to prepare fusion proteins A-P and A2-Q. This assay is based on the principle that binding between proteins P and Q of interest restores the function of the functional protein A, so that detecting its activity allows interaction between the proteins P and Q to be detected. For example, β-lactamase can be utilized as the functional protein. A PCA assay using β-lactamase will now be described.

β-Lactamase is a β-lactam ring-cleaving enzyme derived from bacteria. β-Lactamase is cleaved into an N-terminal α197 fragment (residues 25-197) and a C-terminal Ω198 fragment (residues 198-288), which are respectively expressed as fusion proteins with the proteins of interest. The β-lactamase protein regains its conformation and exhibits activity only when these two bind together. The β-lactamase activity is detected using the cell permeable fluorescent probe CCF2/AM (CCF2 acetoxymethyl ester). CCF2/AM has a structure wherein two different fluorescent substances, coumarin and fluorescein, are bound at either end of a cephalosporin molecule, and it exhibits intramolecular FRET (fluorescence resonance energy transfer) with coumarin as the donor and fluorescein as the acceptor. That is, excitation of coumarin with 409 nm light causes emission of 520 nm fluorescence from fluorescein. If CCF2 is degraded by the β-lactamase activity, however, the two fluorescent substances dissociate and FRET is not observed, and whereas coumarin emits its original fluorescence at 447 nm by excitation with 409 nm light. Measurement of the fluorescence intensity at 447 nm permits assay of β-lactamase activity, or in other words, is allows measurement of the strength of interaction between the proteins of interest.

The screening method of the present invention utilizing a PCA assay may therefore be performed by the following procedure. Cells are allowed to express fusion proteins of two functional protein fragments A1 and A2 fused with either p53 or NEDL1 and cultured either in the presence or in the absence of a test compound. The respective functional protein activities in the cultured cells are assayed, and the test compound is determined to be a pro-apoptotic compound if the functional protein activity in the cells cultured in the presence of the test compound is greater than the functional protein activity in the cells cultured in the absence of the test compound.

Another method for screening pro-apoptotic compounds according to the invention comprises a step of culturing cells expressing p53 and NEDL1 in the presence and in the absence of a test compound, a step of measuring the interaction between p53 and NEDL1 in the cultured cells, and a step of determining the test compound to be a pro-apoptotic compound if the interaction between p53 and NEDL1 in the cultured cells in the presence of the test compound is stronger than the interaction between p53 and NEDL1 in the cultured cells in the absence of the test compound. Measurement of interaction may be accomplished using an assay system for protein-protein interaction that is generally known to those skilled in the art, and immunoprecipitation may be mentioned as an example thereof. A screening method using immunoprecipitation will now be described.

First, cells expressing p53 and NEDL1 are prepared. The cells may be prepared by, for example, subjecting p53-expressing cells such as human neuroblastoma SH-SY5Y cells or human osteosarcoma U2OS cells to stress by treatment with an anticancer agent such as cisplatin, to induce NEDL1 expression. Alternatively, the cells may be prepared by introducing the NEDL1 gene into p53-expressing cells. The cells are cultured both in the presence and in the absence of a test compound.

Interaction between p53 and NEDL1 in the respective cultured cells is then assayed. For the interaction assay, the cultured cells are first pulverized to prepare cell lysates. Although whole cell lysates may be used, it is preferred to use cell lysates from nuclear fractions since interaction between p53 and NEDL1 occurs in the nucleus. An antibody for either the p53 or NEDL1 molecule is added to the prepared cell lysates to perform immunoprecipitation. The obtained precipitate (which contains p53/NEDL1 complexes) is then used in an immunological method (e.g., immunoblotting) with antibody for the other molecule to detect and quantify the p53/NEDL1 complexes, thus allowing assay of interaction between p53 and NEDL1.

The compound may be determined to be a pro-apoptotic compound if the results of the assay indicate that the interaction between p53 and NEDL1 in the cells cultured in the presence of the test compound is stronger (the amount of the protein complex formed is greater) than the interaction between p53 and NEDL1 in the cells cultured in the absence of the test compound.

(Methods for Screening Anti-Apoptotic Compounds)

One method for screening anti-apoptotic compounds according to the invention comprises a step of measuring the interaction between p53 and NEDL1 in the presence and in the absence of a test compound, and a step of determining the test compound to be an anti-apoptotic compound if the interaction between p53 and NEDL1 in the presence of the test compound is weaker than the interaction between p53 and NEDL1 in the absence of the test compound. Measurement of interaction may be accomplished using an assay system for protein-protein interaction that is generally known to those skilled in the art, and the yeast two-hybrid and PCA methods may be mentioned as examples thereof.

This screening method utilizing the yeast two-hybrid assay is performed as follows. Specifically, yeasts are allowed to express either p53 or NEDL1 as bait and the other as prey and cultured both in the presence and in the absence of a test compound. The respective transcriptional activities of reporter genes in the cultured yeasts (which represent the strength of interaction between p53 and NEDL1) are assayed. The test compound can be determined as an anti-apoptotic compound if the transcriptional activity in the presence of the test compound is lower than the transcriptional activity in the absence of the test compound.

This screening method utilizing the PCA assay is performed as follows. Cells are allowed to express fusion proteins of two functional protein fragments A1 and A2 fused with either p53 or NEDL1 and cultured either in the presence or in the absence of a test compound. The respective functional protein activities in the cultured cells are assayed, and the test compound is determined to be an anti-apoptotic compound if the functional protein activity in the cells cultured in the presence of the test compound is lower than the functional protein activity in the cells cultured in the absence of the test compound.

Another method for screening anti-apoptotic compounds according to the invention comprises a step of culturing cells expressing p53 and NEDL1 in the presence and in the absence of a test compound, a step of measuring the interaction between p53 and NEDL1 in the respective cultured cells is assayed, and a step of determining the test compound to be an anti-apoptotic compound if the interaction between p53 and NEDL1 in the cells cultured in the presence of the test compound is weaker than the interaction between p53 and NEDL1 in the cells cultured in the absence of the test compound. Measurement of interaction may be accomplished using an assay system for protein-protein interaction that is generally known to those skilled in the art, and immunoprecipitation may be mentioned as an example thereof.

This screening method utilizing immunoprecipitation is performed as follows. First, cells expressing p53 and NEDL1 are prepared in the manner described above. The cells are cultured both in the presence and in the absence of a test compound. Interaction between p53 and NEDL1 in the respective cultured cells is then assayed. The interaction assay is also conducted in the manner described above. The compound may be determined to be an anti-apoptotic compound if the results of the assay indicate that the interaction between p53 and NEDL1 in the cells cultured in the presence of the test compound is weaker (the amount of the protein complex formed is lower) than the interaction between p53 and NEDL1 in the cells cultured in the absence of the test compound.

(Method of Determining Neurodegenerative Disease Malignancy)

The method of determining neurodegenerative disease malignancy according to the invention comprises a step of measuring interaction between p53 and NEDL1 in neurons taken from a neurodegenerative disease subject, and a step of determining the malignancy of the neurodegenerative disease to be higher with stronger interaction between p53 and NEDL1.

As specific examples of target neurodegenerative diseases there may be mentioned ALS, Alzheimer's disease and Parkinson's disease, although there is no limitation to these. The neurons may be taken from the neurodegenerative disease subject by a method known to those skilled in the art. A method of assaying interaction between p53 and NEDL1 mentioned above (for example, immunoprecipitation) is used to assay the interaction between them (corresponding to protein complex formation in the case of immunoprecipitation), and the malignancy of the neurodegenerative disease is evaluated based on the strength of the interaction. For example, the malignancy of the neurodegenerative disease may be evaluated based on how much stronger the interaction is than the interaction between p53 and NEDL1 in neurons taken from a healthy subject, as a reference standard.

EXAMPLES

The present invention will now be explained in greater detail with reference to examples, with the understanding that the invention is not meant to be limited to these examples.

(Experimental Materials)

The p21$^{WAF1}$ and Bax luciferase reporters were provided by Dr. B. Vogelstein of Johns Hopkins University. The TUNEL staining system was purchased from Roche, the pCDNA3 was purchased from Invitrogen, the Luciferase assay system was purchased from Promega, the cisplatin (CDDP) and G418 were purchased from Sigma, and the anti-p53 antibody, anti-actin antibody, anti-p21$^{WAF1}$ antibody and anti-Xpress antibody were purchased from Oncogene Research Products, Sigma, Santa Cruz Biotechnologies and Invitrogen, respectively. The normal rabbit serum was purchased from Jackson ImmunoResearch.

The primers used for PCR were as follows.

```
                                       (SEQ ID NO: 1)
NEDL1: 5'-CCGATTTGAGATCACTTCCTCC-3'
                                       (SEQ ID NO: 2)
       5'-CCGCTTTCCATCAGGTTGTT-3'
                                       (SEQ ID NO: 3)
GAPDH: 5'-ACCTGACCTGCCGTCTAGAA-3'
                                       (SEQ ID NO: 4)
       5'-TCCACCACCCTGTTGCTGTA-3'
                                       (SEQ ID NO: 5)
p53:   5'-ATTTGATGCTGTCCCCGGACGATATTGAAC-3'
                                       (SEQ ID NO: 6)
       5'-ACCCTTTTTGGACTTCAGGTGGCTGGAGTG-3'
                                       (SEQ ID NO: 7)
p21:   5'-ATGAAATTCACCCCCTTTCC-3'
                                       (SEQ ID NO: 8)
       5'-CCCTAGGCTGTGCTCACTTC-3'
                                       (SEQ ID NO: 9)
NEDL2: 5'-ACGTGAGTGGGTACCTCCAG-3'
                                       (SEQ ID NO: 10)
       5'-CCTCAGAAACTGGCCCATTA-3'
                                       (SEQ ID NO: 11)
NEDD4: 5'-TTCCGAAGAAAGTTGAAGAAGC-3'
                                       (SEQ ID NO: 12)
       5'-CTCTGGCAACTCCTCCATAATC-3'
```

(Experiment Procedure)

The RT-PCR, Western blotting, immunoprecipitation, luciferase reporter assay and cell fractionation were performed according to the procedure described in Ando et al., J. Biol. Chem., 279: 25549-25561, 2004. Colony formation was performed according to the procedure described in Ozaki et al., Cancer Res., 59: 5902-5907, 1999.

Example 1

Inducing Apoptosis of SH-SY5Y Cells by Cisplatin Treatment

Figure 1:
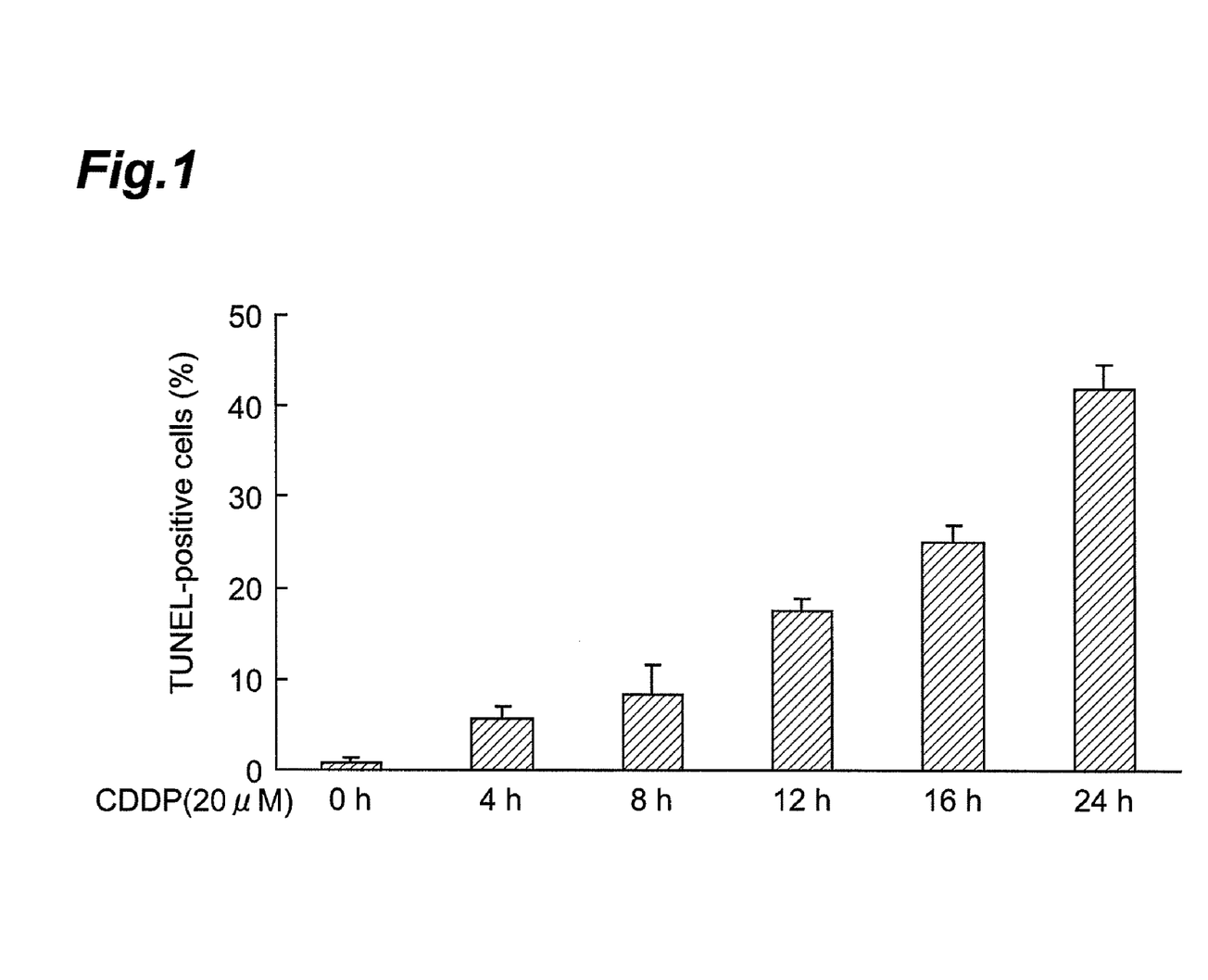
FIG. 1 is a graph showing the proportion of TUNEL-positive cells among cisplatin treated SH-SY5Y cells.

SH-SY5Y cells were cultured in the presence of cisplatin (final concentration: 20 μM). The cells were fixed with paraformaldehyde at prescribed time points after the start of culturing and subjected to TUNEL staining, and the TUNEL-positive cells were counted. FIG. 1 shows the proportion of TUNEL-positive cells. The extent of cell death by cisplatin was detected.

Example 2

Expression Analysis by RT-PCR

Figure 2:
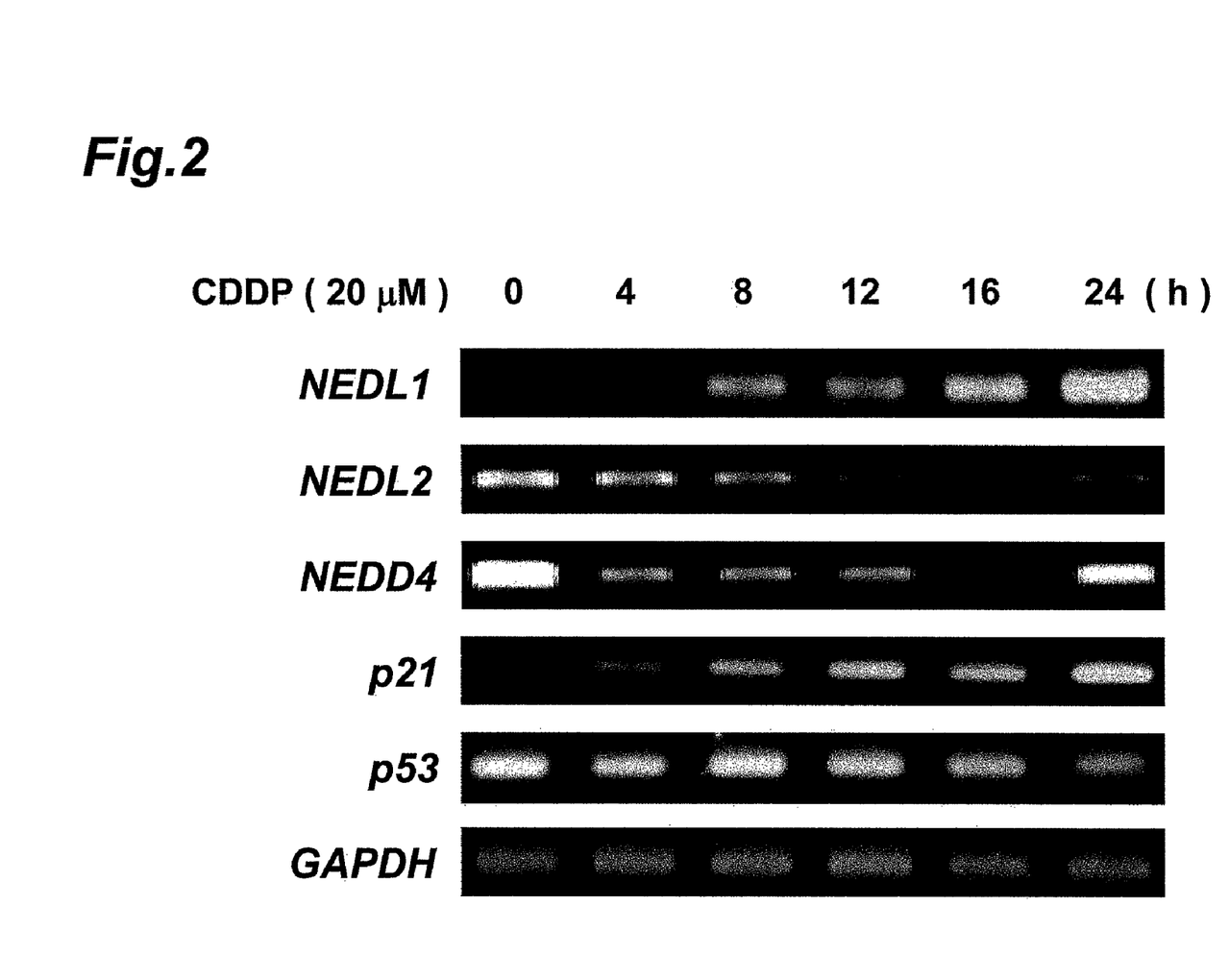
FIG. 2 shows the results of RT-PCR analysis of RNA from cisplatin treated SH-SY5Y cells.

Under the same conditions as in Example 1, SH-SY5Y cells were treated with cisplatin and cells were recovered at a prescribed time point, after which the total RNA was extracted and expression of the NEDL1, NEDL2, NEDD4, p21$^{WAF1}$ and p53 genes was analyzed by RT-PCR. GAPDH was used as an expression level control. FIG. 2 shows the results of analysis by RT-PCR. Expression of NEDL1 was found to be induced in response to cisplatin.

Example 3

Expression Analysis by Western Blotting

Figure 3:
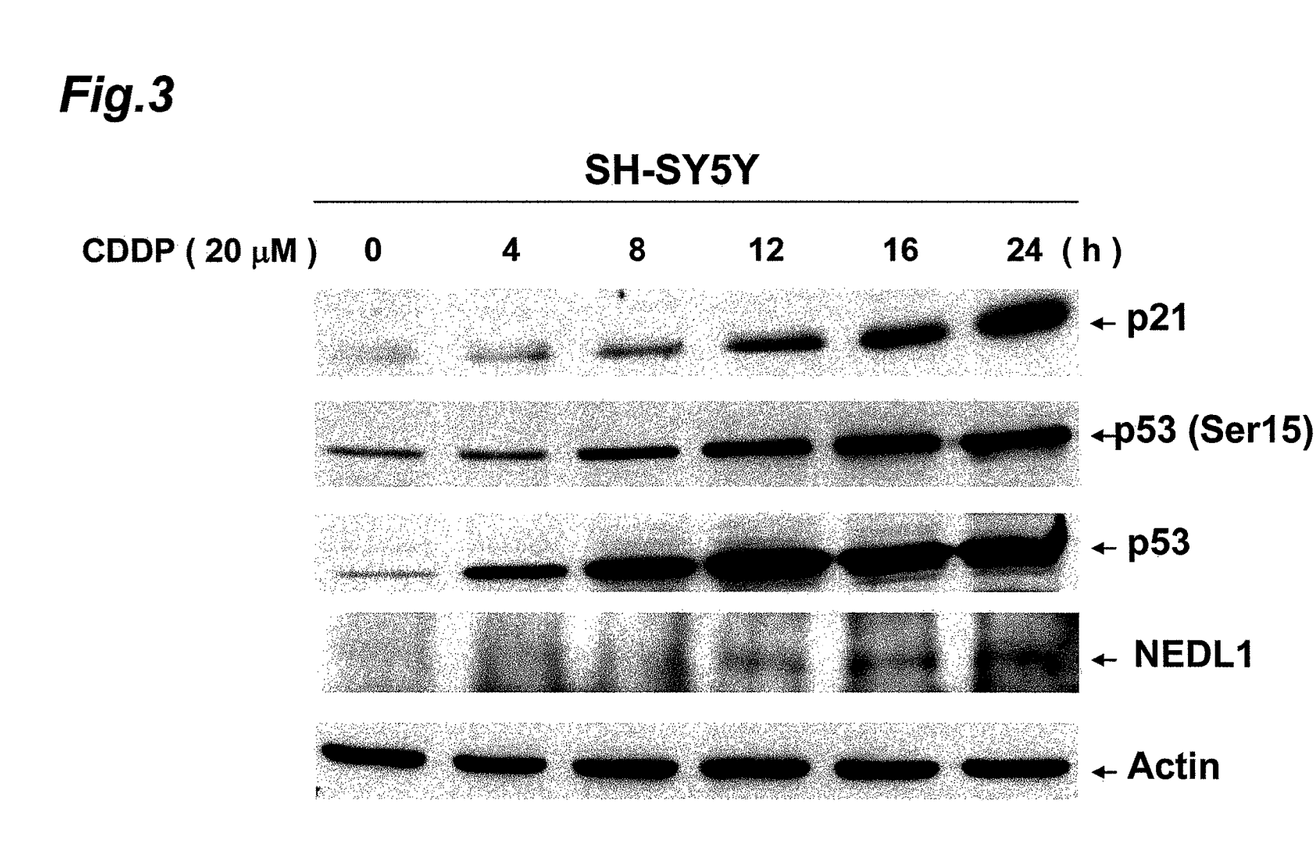
FIG. 3 shows the results of Western blotting of protein from cisplatin treated SH-SY5Y cells.

Under the same conditions as in Example 1, SH-SY5Y cells were treated with cisplatin and cells were recovered at a prescribed time point, after which the total protein was extracted and the expression of p21$^{WAF1}$, phosphorylated p53

(p53 (Ser 15)), p53 and NEDL1 was analyzed by Western blotting. Actin was used as an expression level control. FIG. 3 shows the results of analysis by Western blotting. Expression of $p21^{WAF1}$, phosphorylated p53, p53 and NEDL1 was found to be induced in response to cisplatin.

Example 4

Colony Forming Experiment

Figure 4:
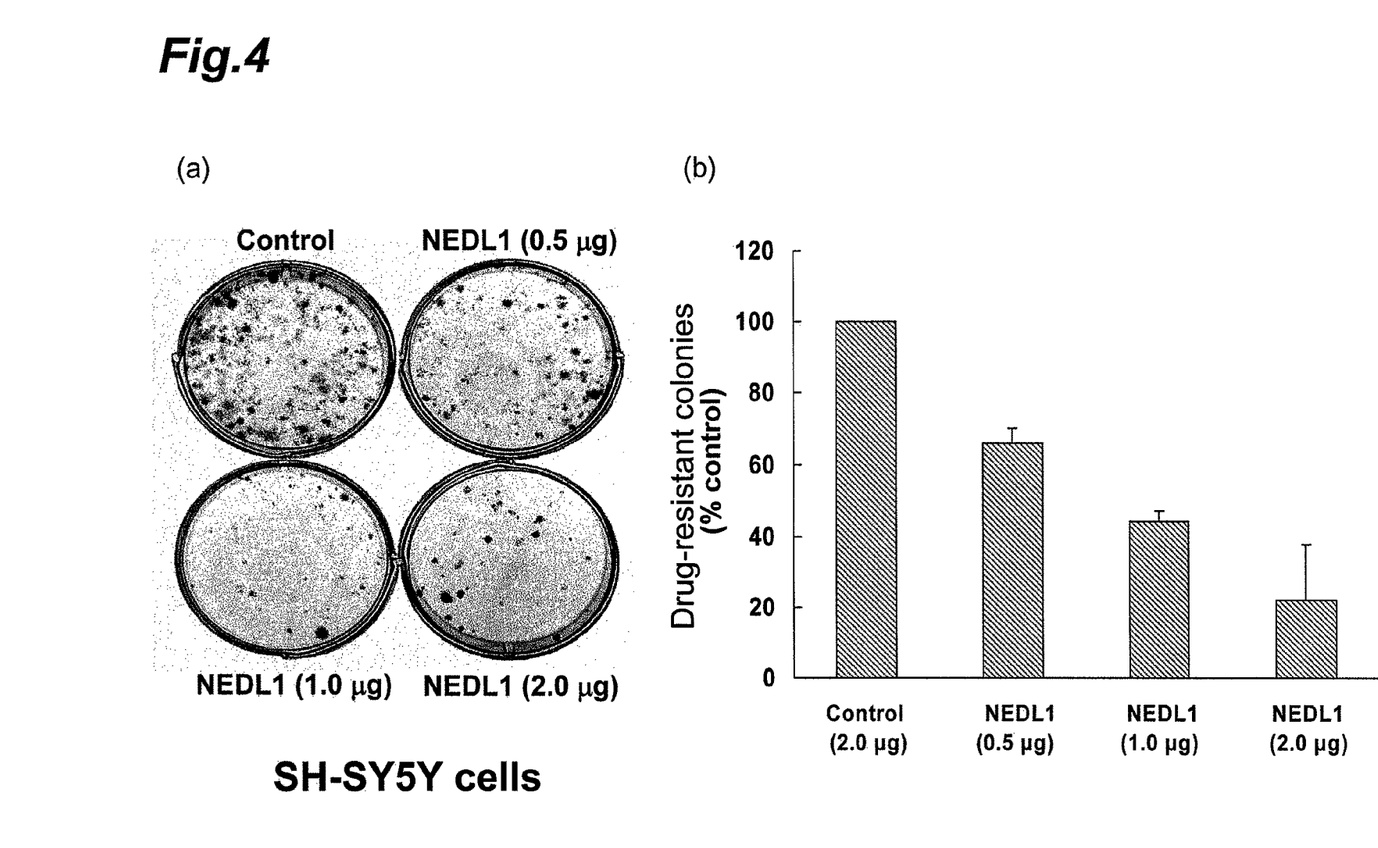
FIG. 4 is a photograph and graph showing the results of a colony forming experiment with SH-SY5Y cells.
Figure 5:
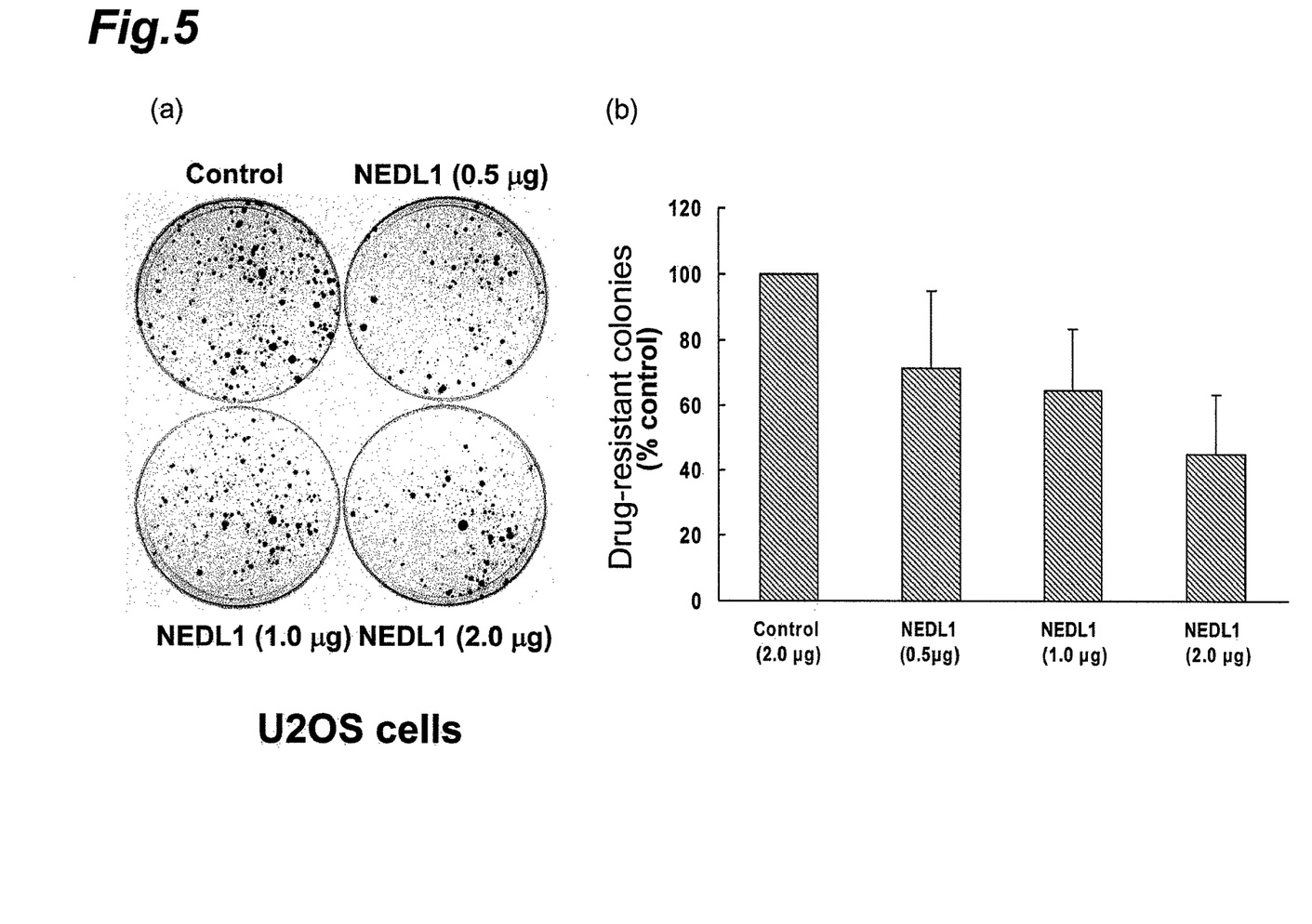
FIG. 5 is a photograph and graph showing the results of a colony forming experiment with U2OS cells.
Figure 6:
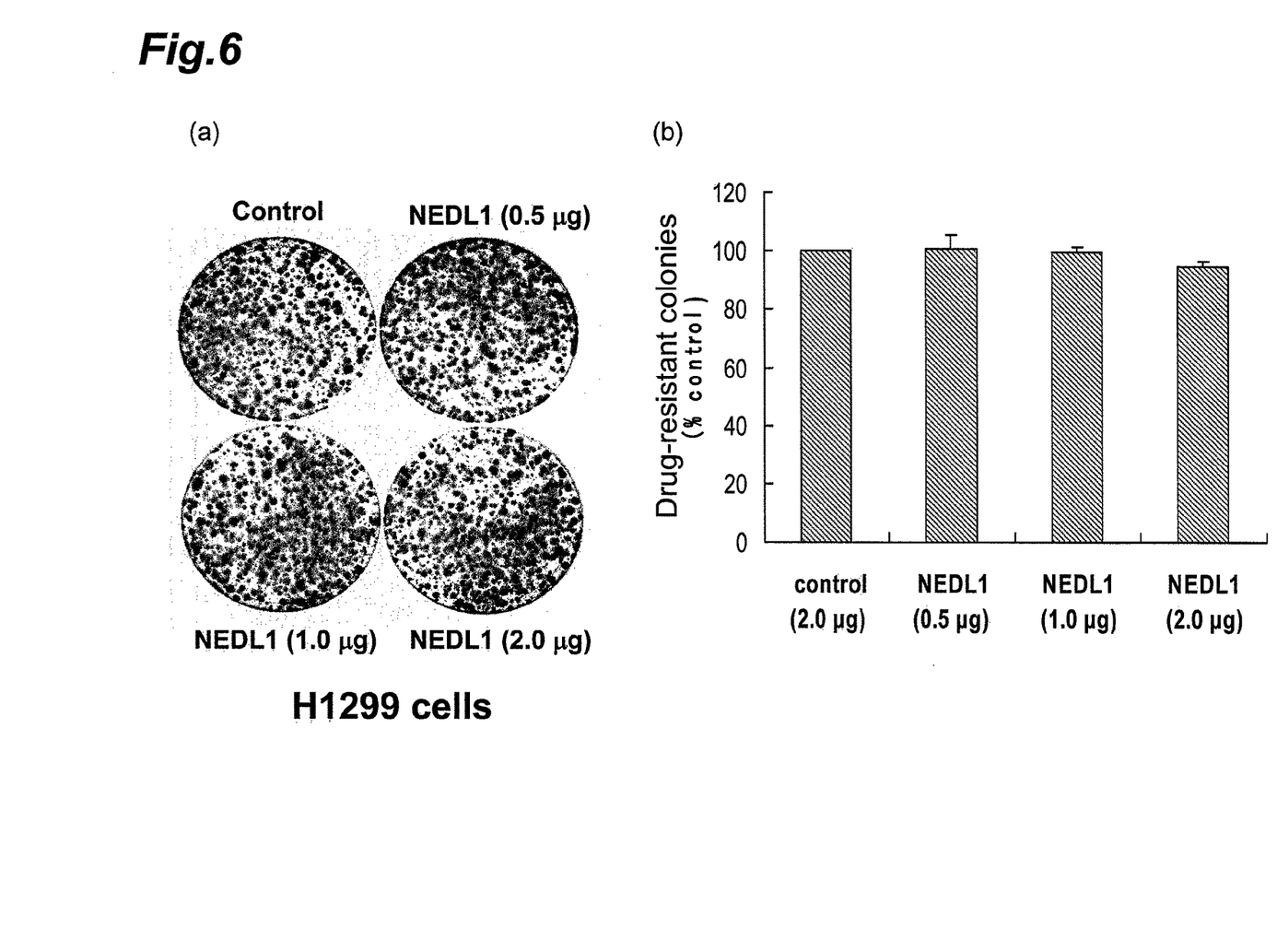
FIG. 6 is a photograph and graph showing the results of a colony forming experiment with H1299 cells.

In order to examine whether or not apoptosis is induced by NEDL1, NEDL1-encoding expression plasmids were transfected into SH-SY5Y, U2OS and H1299 cells (using pCDNA3 as a control). At 48 hours after gene transfection, the cells were transplanted into G418-containing medium and cultured for 14 days, and numbers of colonies exhibiting G418 resistance were counted. The results for SH-SY5Y, U2OS and H1299 cells are shown in FIGS. 4, 5 and 6. NEDL1 was found to cause a reduction in the number of G418-resistant colonies in the SH-SY5Y and U2OS cells. In the H1299 cells which did not express p53, however, NEDL1 did not cause a reduction in the number of G418-resistant colonies.

Example 5

Luciferase Reporter Assay

Figure 7:
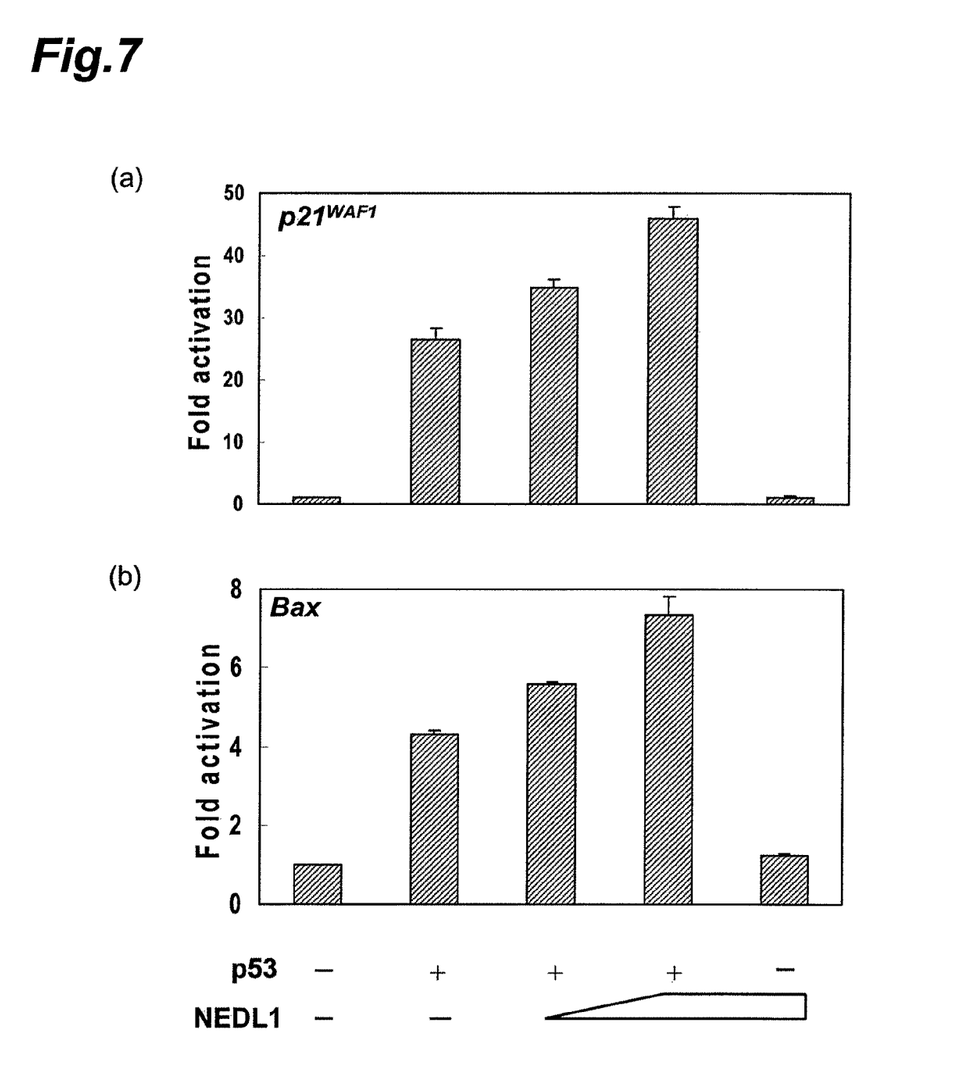
FIG. 7 is a graph showing the increase in transcription activation of p53.

In order to examine the effect of NEDL1 on the transcriptional activation potential of p53, expression plasmids coding for p53 and NEDL1 and luciferase expression plasmids containing the promoter region of $p21^{WAF1}$ or Bax were transfected into H1299 cells. The cells were recovered 48 hours after gene transfection and the luciferase activities were assayed. As shown in FIG. 7, NEDL1 augmented the transcription activation potential of p53.

Example 6

Confirming P53/NEDL1 Complex Formation

Figure 8:
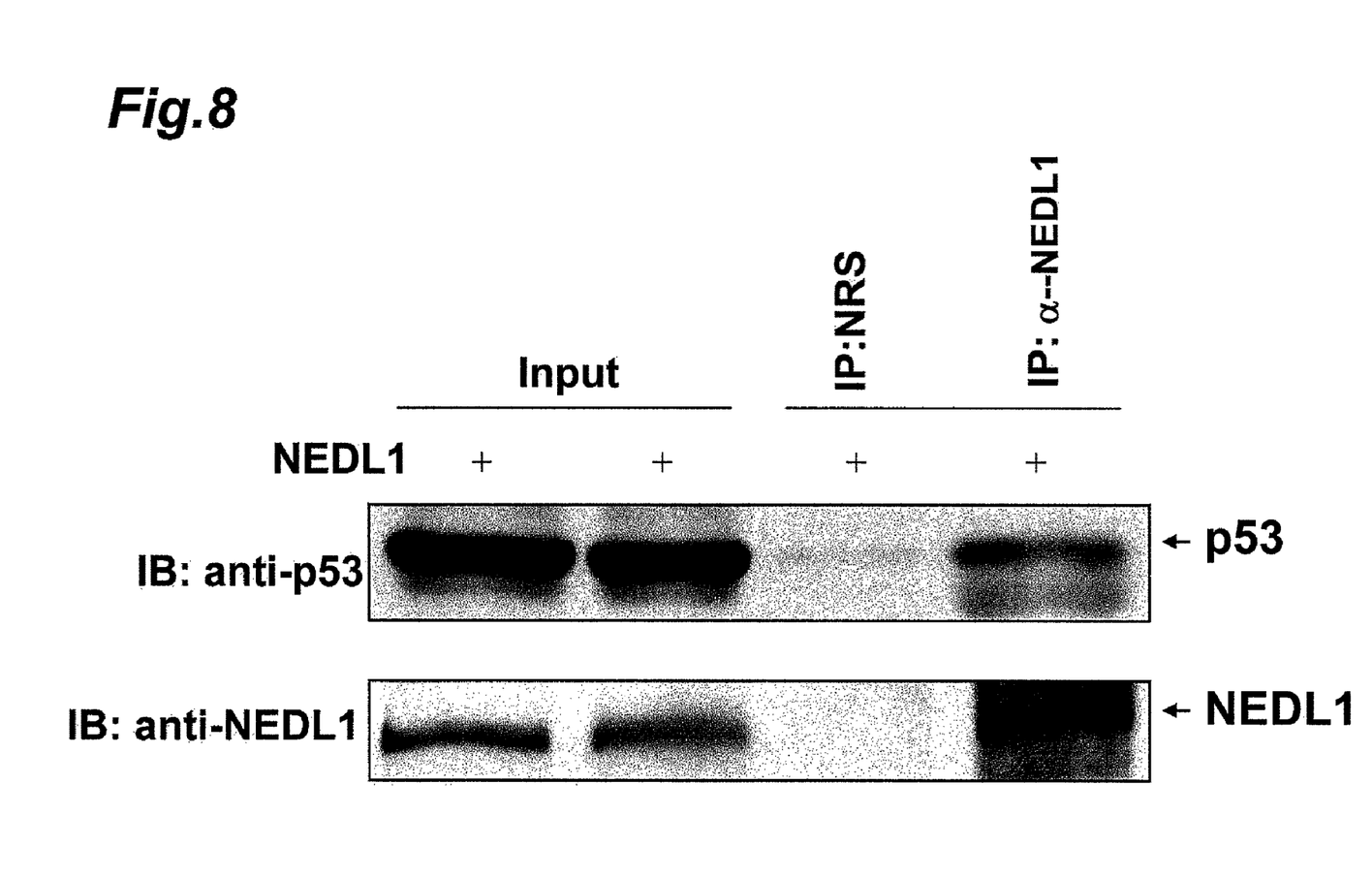
FIG. 8 shows the results of immunoprecipitation and immunoblotting of COST cells transfected with NEDL1-expressing plasmids. IP represents the antibody used for immunoprecipitation, and IB represents the antibody used for immunoblotting.

An expression plasmid coding for NEDL1 was transfected into endogenously p53-expressing COS7 cells. The cells were recovered 48 hours after gene transfection, the total protein was extracted and immunoprecipitated with normal rabbit antibody (NRS) or anti-NEDL1 antibody, and the immunoprecipitation product was analyzed by Western blotting. The results are shown in FIG. 8. Formation of NEDL1 and endogenous p53 complexes was confirmed.

Example 7

Confirming p53/NEDL1 Complex Formation in Cell Nuclei

Figure 9:
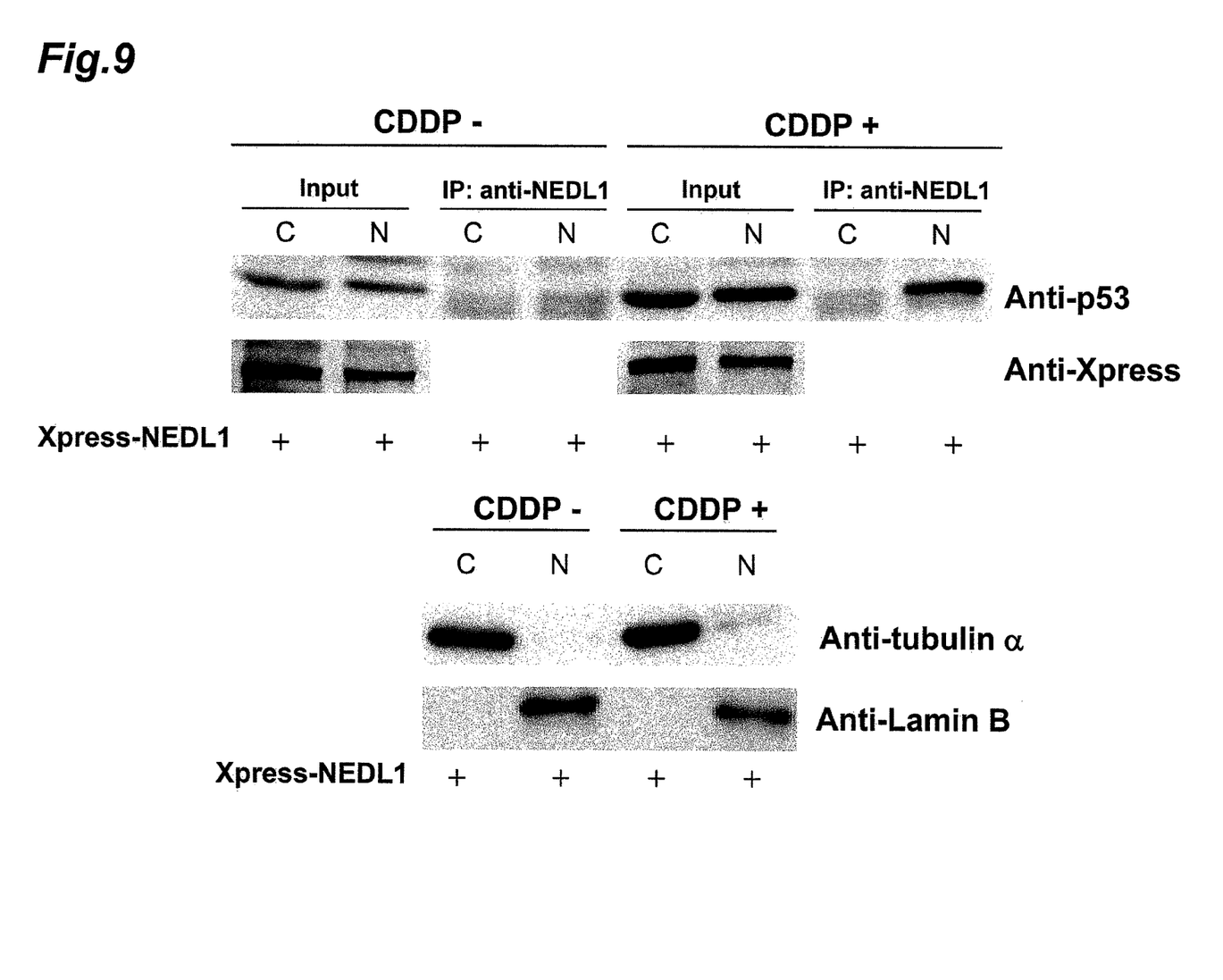
FIG. 9 shows the results of immunoblotting of cytoplasmic (C) and nuclear (N) fractions of cisplatin-treated and untreated U2OS cells.
Figure 10:
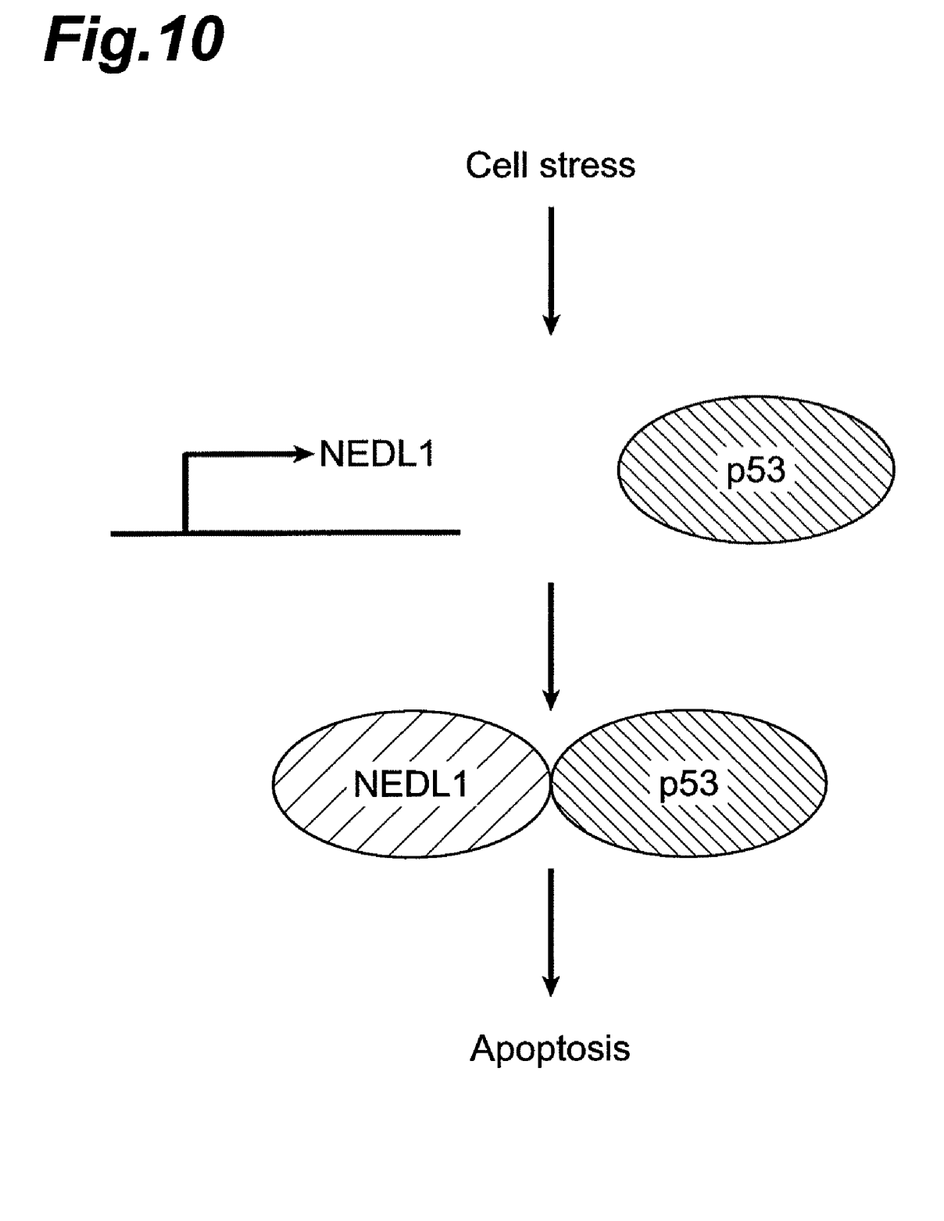
FIG. 10 is a schematic representation of the relationship between NEDL1 and p53. In response to various types of stress, p53 is activated by physical binding with NEDL1 in the nucleus, inducing p53-dependent cell death.

An Xpress-tagged NEDL1-coding expression plasmid was transfected into U2OS cells. At 24 hours after gene transfection, the cells were divided into a cisplatin treated group and a non-treated group, and culturing was continued for 24 hours in the presence or in the absence of cisplatin. The cells were recovered and fractionated into cytoplasmic (C) and nuclear (N) fractions and then immunoprecipitated with anti-NEDL1 antibody, and the immunoprecipitation product was analyzed by Western blotting. Tubulin α and lamin B were used as cell fractionation markers. The results are shown in FIG. 9. Formation of p53/NEDL1 complexes in the cell nuclei was confirmed.

INDUSTRIAL APPLICABILITY

The screening methods of the present invention provide pro- and anti-apoptotic compounds with totally different action mechanisms than currently known. Such compounds can serve as drugs effective for the treatment and prevention of cancer or neurodegenerative diseases.

Moreover, the method of determining malignancy of neurodegenerative diseases according to the invention provides a method of determining neurodegenerative disease malignancy based on different criteria of determination than currently known.

The invention claimed is:

1. A method for screening pro-apoptotic compounds comprising:
   a step of measuring the interaction between p53 and NEDL1 in the presence and in the absence of a test compound; and
   a step of determining the test compound to be a pro-apoptotic compound if the interaction between p53 and NEDL1 in the presence of the test compound is stronger than the interaction between p53 and NEDL1 in the absence of the test compound.

2. A method for screening pro-apoptotic compounds comprising:
   a step of culturing cells expressing p53 and NEDL1 in the presence and in the absence of a test compound;
   a step of measuring the interaction between p53 and NEDL1 in the cultured cells; and
   a step of determining the test compound to be a pro-apoptotic compound if the interaction between p53 and NEDL1 in the cultured cells in the presence of the test compound is stronger than the interaction between p53 and NEDL1 in the cultured cells in the absence of the test compound.

3. A method for screening anti-apoptotic compounds comprising:
   a step of measuring the interaction between p53 and NEDL1 in the presence and in the absence of a test compound; and
   a step of determining the test compound to be an anti-apoptotic compound if the interaction between p53 and NEDL1 in the presence of the test compound is weaker than the interaction between p53 and NEDL1 in the absence of the test compound.

4. A method for screening anti-apoptotic compounds comprising:
   a step of culturing cells expressing p53 and NEDL1 in the presence and in the absence of a test compound;
   a step of measuring the interaction between p53 and NEDL1 in the cultured cells; and
   a step of determining the test compound to be an anti-apoptotic compound if the interaction between p53 and NEDL1 in the cultured cells in the presence of the test compound is weaker than the interaction between p53 and NEDL1 in the cultured cells in the absence of the test compound.

* * * * *

SEQUENCE LISTING

```
<160> NUMBER OF SEQ ID NOS: 12

<210> SEQ ID NO 1
<211> LENGTH: 22
<212> TYPE: DNA
<213> ORGANISM: Artificial Sequence
<220> FEATURE:
<223> OTHER INFORMATION: NEDL1 primer

<400> SEQUENCE: 1
ccgatttgag atcacttcct cc                                          22

<210> SEQ ID NO 2
<211> LENGTH: 20
<212> TYPE: DNA
<213> ORGANISM: Artificial Sequence
<220> FEATURE:
<223> OTHER INFORMATION: NEDL1 primer

<400> SEQUENCE: 2
ccgctttcca tcaggttgtt                                             20
```

```
<210> SEQ ID NO 3
<211> LENGTH: 20
<212> TYPE: DNA
<213> ORGANISM: Artificial Sequence
<220> FEATURE:
<223> OTHER INFORMATION: GAPDH primer

<400> SEQUENCE: 3
acctgacctg ccgtctagaa                                              20

<210> SEQ ID NO 4
<211> LENGTH: 20
<212> TYPE: DNA
<213> ORGANISM: Artificial Sequence
<220> FEATURE:
<223> OTHER INFORMATION: GAPDH primer

<400> SEQUENCE: 4
tccaccaccc tgttgctgta                                              20

<210> SEQ ID NO 5
<211> LENGTH: 30
<212> TYPE: DNA
<213> ORGANISM: Artificial Sequence
<220> FEATURE:
<223> OTHER INFORMATION: p53 primer

<400> SEQUENCE: 5
atttgatgct gtccccggac gatattgaac                                   30

<210> SEQ ID NO 6
<211> LENGTH: 30
<212> TYPE: DNA
<213> ORGANISM: Artificial Sequence
<220> FEATURE:
<223> OTHER INFORMATION: p53 primer

<400> SEQUENCE: 6 acccttttg gacttcaggt ggctggagtg                                    30

<210> SEQ ID NO 7
<211> LENGTH: 20
<212> TYPE: DNA
<213> ORGANISM: Artificial Sequence
<220> FEATURE:
<223> OTHER INFORMATION: p21 primer

<400> SEQUENCE: 7
atgaaattca cccccttcc                                               20

<210> SEQ ID NO 8
<211> LENGTH: 20
<212> TYPE: DNA
<213> ORGANISM: Artificial Sequence
<220> FEATURE:
<223> OTHER INFORMATION: p21 primer

<400> SEQUENCE: 8
ccctaggctg tgctcacttc                                              20

<210> SEQ ID NO 9
<211> LENGTH: 20
<212> TYPE: DNA
<213> ORGANISM: Artificial Sequence
<220> FEATURE:
<223> OTHER INFORMATION: NEDL2 primer

<400> SEQUENCE: 9
```

```
acgtgagtgg gtacctccag                                              20

<210> SEQ ID NO 10
<211> LENGTH: 20
<212> TYPE: DNA
<213> ORGANISM: Artificial Sequence
<220> FEATURE:
<223> OTHER INFORMATION: NEDL2 primer

<400> SEQUENCE: 10
cctcagaaac tggcccatta                                              20

<210> SEQ ID NO 11
<211> LENGTH: 22
<212> TYPE: DNA
<213> ORGANISM: Artificial Sequence
<220> FEATURE:
<223> OTHER INFORMATION: NEDD4 primer

<400> SEQUENCE: 11
ttccgaagaa agttgaagaa gc                                           22

<210> SEQ ID NO 12
<211> LENGTH: 22
<212> TYPE: DNA
<213> ORGANISM: Artificial Sequence
<220> FEATURE:
<223> OTHER INFORMATION: NEDD4 primer

<400> SEQUENCE: 12
ctctggcaac tcctccataa tc                                           22
```